(12) United States Patent
Kuroda et al.

(10) Patent No.: US 10,850,072 B2
(45) Date of Patent: Dec. 1, 2020

(54) WIRE MEMBER

(71) Applicant: GUNZE LIMITED, Kyoto (JP)

(72) Inventors: Kouji Kuroda, Moriyama (JP); Makoto Kawahara, Moriyama (JP)

(73) Assignee: GUNZE LIMITED, Kyoto (JP)

(*) Notice: Subject to any disclaimer, the term of this patent is extended or adjusted under 35 U.S.C. 154(b) by 0 days.

(21) Appl. No.: 15/523,289

(22) PCT Filed: Nov. 2, 2015

(86) PCT No.: PCT/JP2015/080938
§ 371 (c)(1),
(2) Date: Aug. 7, 2017

(87) PCT Pub. No.: WO2016/072394
PCT Pub. Date: May 12, 2016

(65) Prior Publication Data
US 2018/0014899 A1    Jan. 18, 2018

(30) Foreign Application Priority Data

Nov. 4, 2014 (JP) .................................. 2014-223900

(51) Int. Cl.
*A61M 25/09* (2006.01)
*D07B 1/06* (2006.01)
(Continued)

(52) U.S. Cl.
CPC ............. *A61M 25/09* (2013.01); *A61B 34/71* (2016.02); *D07B 1/06* (2013.01); *D07B 5/005* (2013.01); *A61M 2025/006* (2013.01); *A61M 2025/0062* (2013.01); *A61M 2025/09083* (2013.01); *A61M 2025/09091* (2013.01); *A61M 2025/09108* (2013.01); *A61M 2025/09116* (2013.01);
(Continued)

(58) Field of Classification Search
CPC ......... A61M 25/09–0905; A61M 2025/09008; A61M 2025/09058–09191
See application file for complete search history.

(56) References Cited

U.S. PATENT DOCUMENTS

| | | | | |
|---|---|---|---|---|
| 8,500,657 B2 * | 8/2013 | Brown | .................. | A61M 25/09 600/585 |
| 2015/0306354 A1 * | 10/2015 | Kanetake | .............. | A61M 25/09 604/529 |

FOREIGN PATENT DOCUMENTS

| | | |
|---|---|---|
| EP | 1 707 234 A1 | 10/2006 |
| JP | 2010-011883 A | 1/2010 |

(Continued)

OTHER PUBLICATIONS

International Search Report issued in PCT/JP2015/080938; dated Mar. 8, 2016.

*Primary Examiner* — David J. McCrosky
(74) *Attorney, Agent, or Firm* — Studebaker & Brackett PC

(57) ABSTRACT

A wire member that exhibits an excellent sliding property is provided.

A wire member 1 includes: a core member 2 that has an elongated shape; and a surface-disposed member 3 that is spirally disposed on a surface of the core member 2 so as to leave predetermined spaces along a longitudinal direction of the core member 2. In a cross-sectional view taken along the axis of the core member 2, the front end and the rear end of each of projections 3A formed by the surface-disposed member 3 respectively form contact angles θ1, θ2 each being 5° or greater relative to the surface of the core member 2.

6 Claims, 6 Drawing Sheets

(51) Int. Cl.
  *A61B 34/00* (2016.01)
  *D07B 5/00* (2006.01)
  *A61M 25/00* (2006.01)
(52) U.S. Cl.
  CPC .............. *A61M 2025/09133* (2013.01); *D07B 2201/2007* (2013.01)

(56) References Cited

FOREIGN PATENT DOCUMENTS

| | | | |
|---|---|---|---|
| JP | 2011-194065 | A | 10/2011 |
| JP | 2012-070979 | A | 4/2012 |
| JP | 2012-213667 | A | 11/2012 |
| WO | 2014/091935 | A1 | 6/2014 |

* cited by examiner

[Fig.1]
Longitudinal direction of core member 2
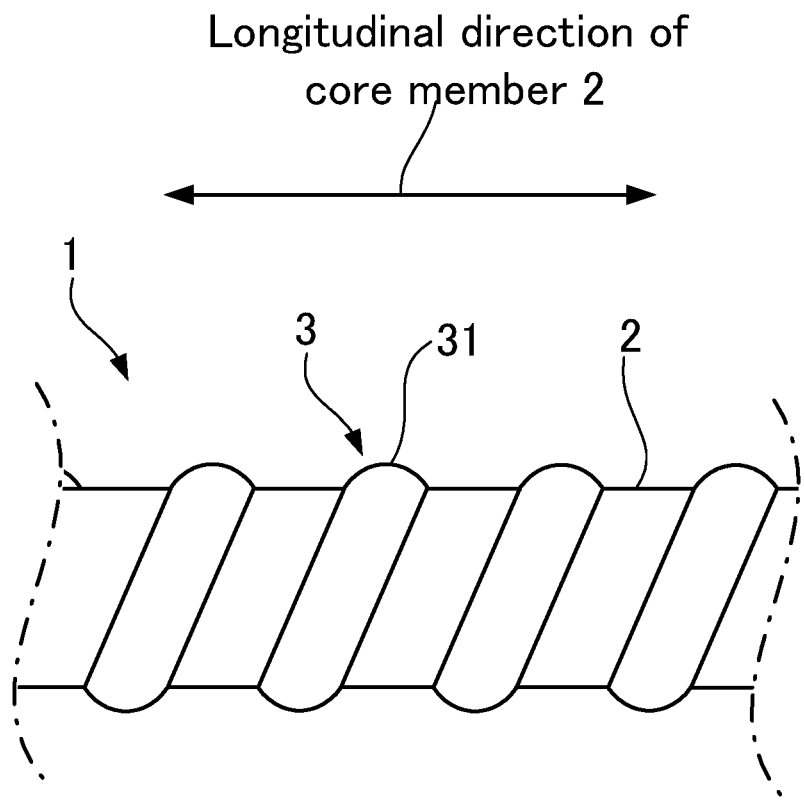
[Fig.2]
Longitudinal direction of core member 2
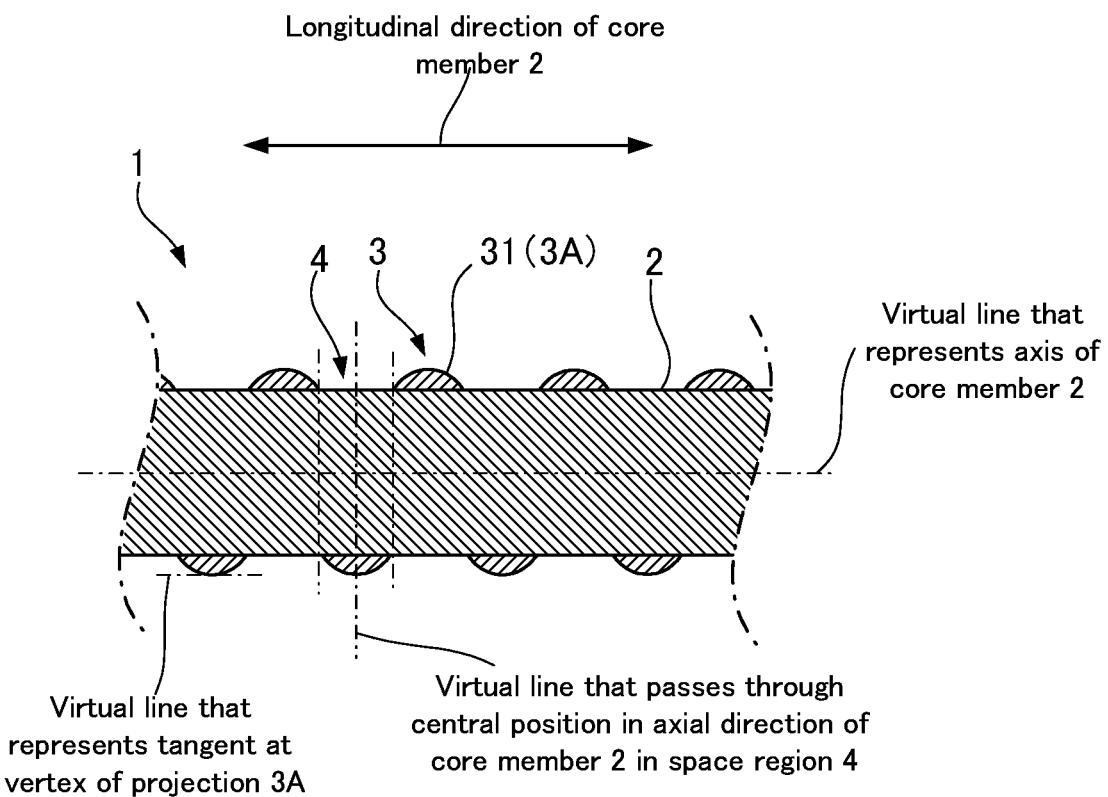
Virtual line that represents axis of core member 2
Virtual line that represents tangent at vertex of projection 3A
Virtual line that passes through central position in axial direction of core member 2 in space region 4

[Fig.3]
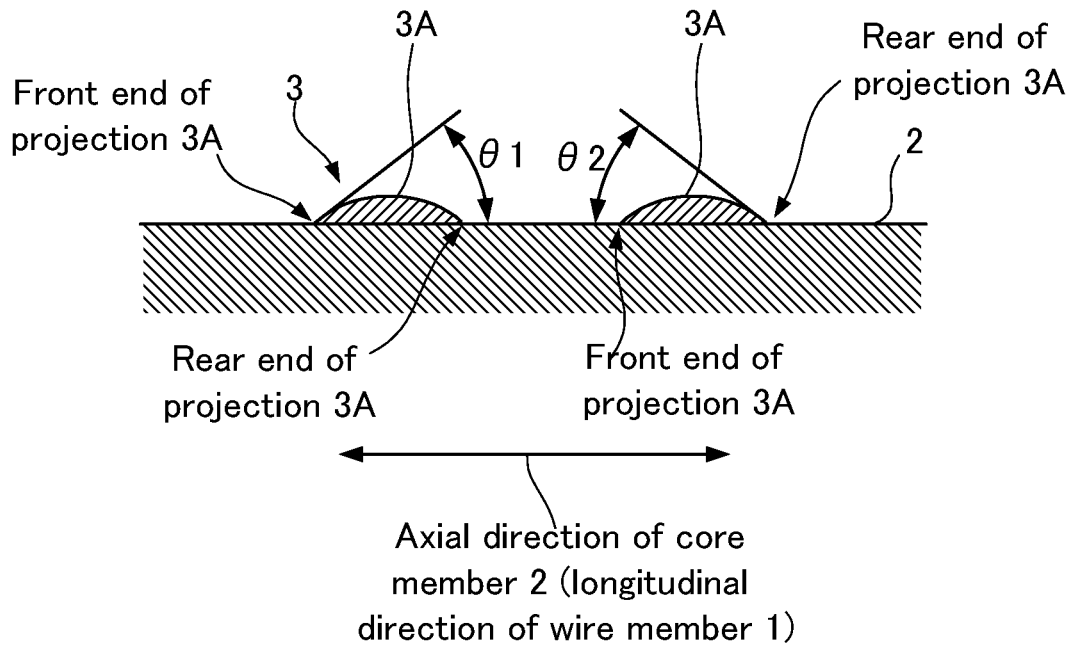
[Fig.4]
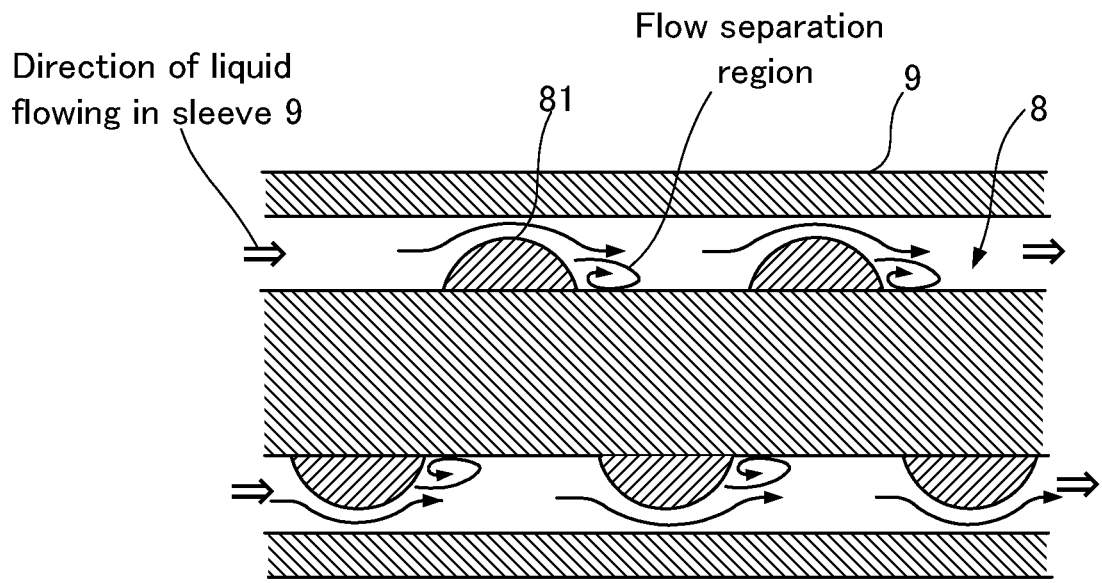

[Fig.5]
Direction of liquid flowing in sleeve 9
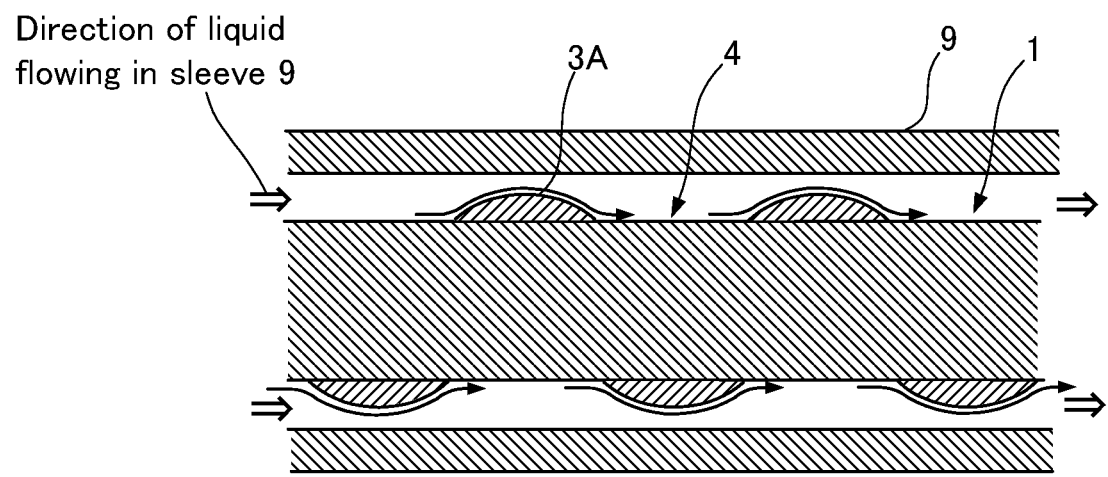

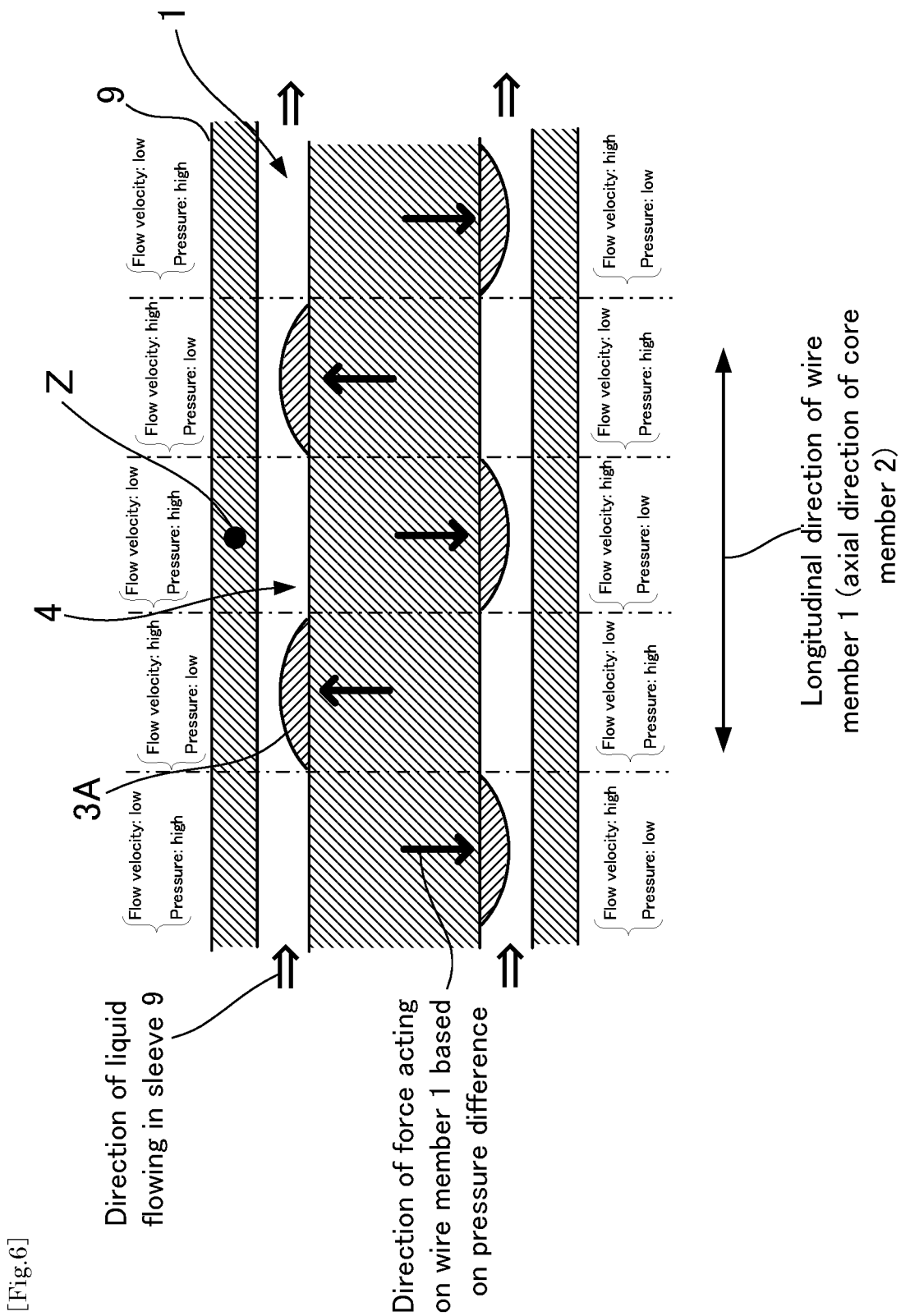

[Fig.7]
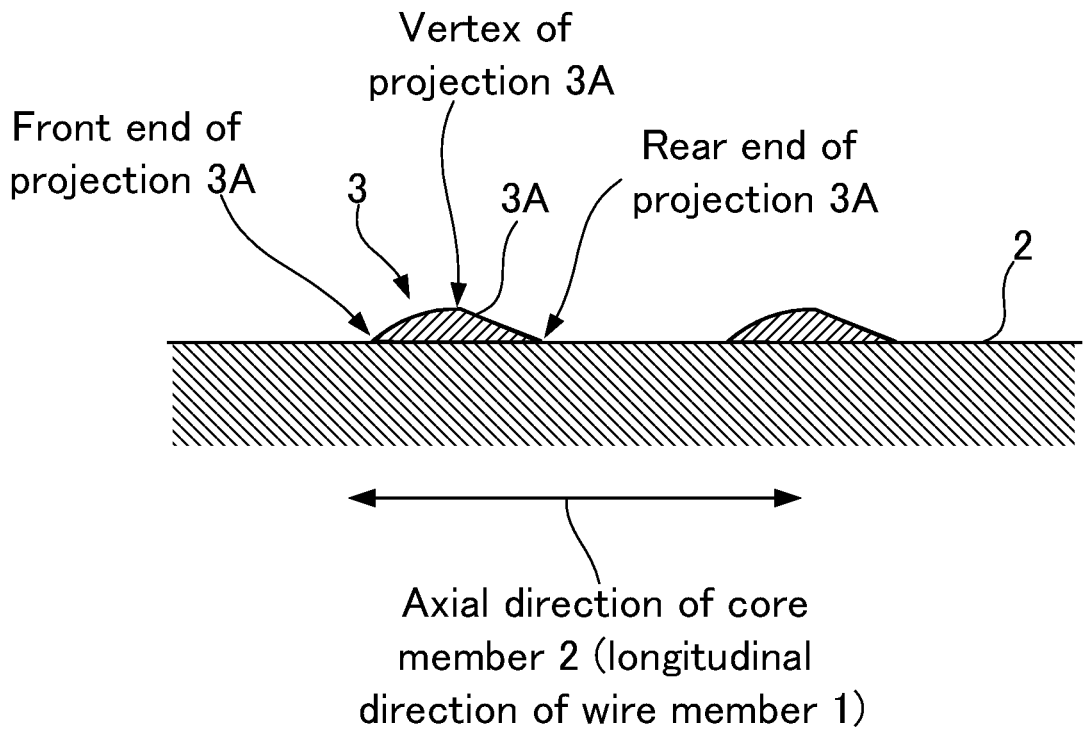
[Fig.8]
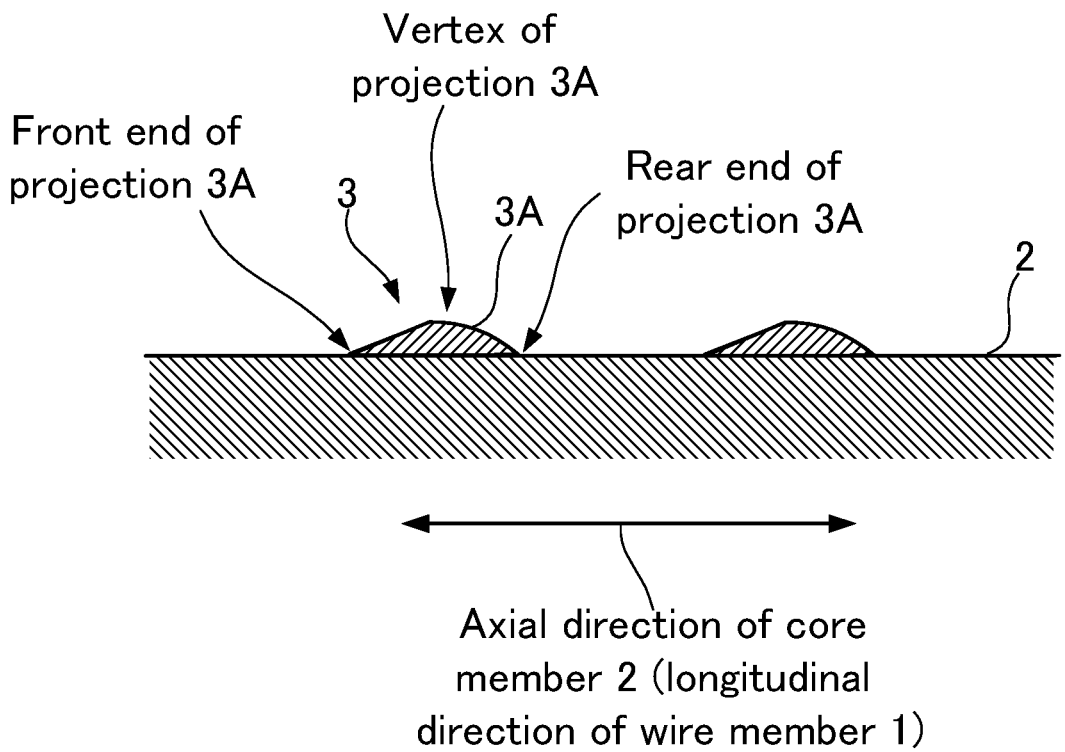

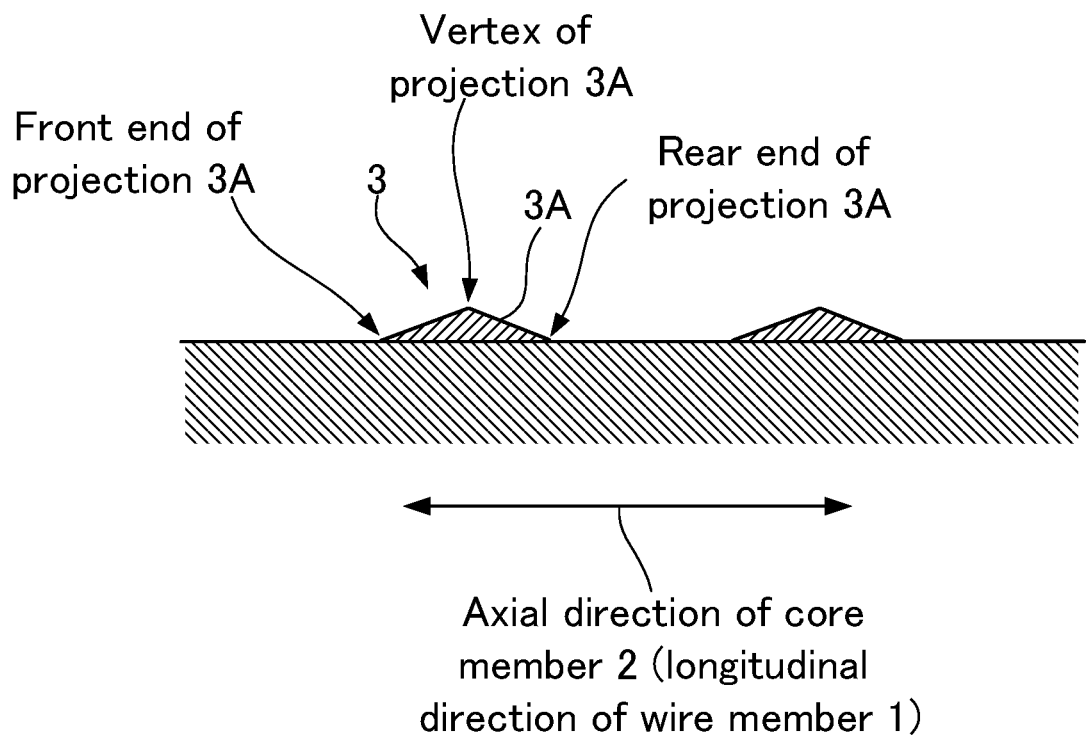

WIRE MEMBER

TECHNICAL FIELD

The present invention relates to a wire member.

BACKGROUND ART

Conventionally, a wire member is used in a manipulation system or a power transmission system of various apparatuses or devices. For example, a wire member is used as a medical guide wire for ensuring safety and reliability in inserting a catheter into heart and blood vessels, a bile duct or the like, or as a driving wire or the like that is inserted into a shaft part of a medical manipulator for driving a distal working part that is disposed at the tip of the shaft part.

A medical guide wire is used as follows. With its tip projected further than the tip of the catheter, the medical guide wire is inserted into a blood vessel, a bile duct or the like. The proximal part of the medical guide wire positioned outside the human body is pushed and pulled while being rotated, so as to cause the medical guide wire to advance inside the blood vessel or the like and to reach together with the catheter the position near the target site. In this state, the catheter is shifted along the medical guide wire. Thus, the tip portion of the catheter is guided to the position near the target site.

A medical manipulator is structured to include, for example: a hollow shaft; a driving wire that is inserted into the shaft; a driving mechanism part that is provided on one end side of the shaft and advances or retracts the driving wire in the axial direction; and a distal working part that is provided on the other end side of the shaft and operated by the advancing or retracting of the wire member. As the distal working part, various kinds of end effectors are known, including a gripper for gripping living tissue, scissors for cutting, the electrode of an electric scalpel for sealing a blood vessel or dissecting/separating tissue planes, a suturing unit having a needle for suturing, and an anastomosing unit for anastomosing intestines.

Such a wire member used as being inserted into a tubular member (a sleeve) such as the catheter or the shaft is required to smoothly advance or retract inside the sleeve, or the sleeve must smoothly advance or retract relative to the wire member. Accordingly, there exists a known wire member in which the outer diameter of the wire member is set to have a dimension that is enough to create a space (a clearance) between the inner surface of the sleeve and the outer circumferential surface of the wire member. Further, for improving the sliding property of the wire member upon any contact with the inner wall of the sleeve, a projection is spirally formed on the surface of a core member of the wire member (e.g., see Patent Document 1).

PRIOR ART DOCUMENT

Patent Document

Patent Document 1: Japanese Unexamined Patent Publication No. 2010-011883

SUMMARY OF THE INVENTION

Problems to be Solved by the Invention

However, when the wire member is used as being inserted into the sleeve, the wire member may be shifted with the sleeve being filled with liquid such as physiological saline, a contrast medium or the like. In such a case, the conventional wire member encounters resistance due to contact with the inner wall of the sleeve and resistance due to the liquid. Thus, there exists a problem that the conventional wire member fails to smoothly advance or retract relative to the sleeve.

The present invention has been made in order to solve such a problem, and an object thereof is to provide a wire member that exhibits an excellent sliding property.

Means for Solving the Problems

The object of the present invention is achieved by providing a wire member including a core member that has an elongated shape and a surface-disposed member that is spirally disposed on a surface of the core member so as to leave predetermined spaces along a longitudinal direction of the core member, wherein in a cross-sectional view taken along an axis of the core member, a front end and a rear end of each of projections formed by the surface-disposed member each form a contact angle of 5° or greater relative to the surface of the core member.

In the wire member, the contact angle is preferably 65° or smaller.

Further, in a cross-sectional view taken along the axis of the core member, the projections on other side with reference to the core member are preferably disposed so as to oppose to space regions each formed between the projections disposed on one side with reference to the core member.

Still further, in a cross-sectional view taken along the axis of the core member, a vertex of each of the projections on other side with reference to the core member is preferably disposed so as to oppose to substantially a center of corresponding one of the space regions in an axial direction of the core member.

Still further, in a cross-sectional view taken along the axis of the core member, a surface of the core member at the space regions is preferably substantially parallel to the axis of the core member.

Still further, in a cross-sectional view taken along the axis of the core member, an angle formed between a tangent at an arbitrary point on a surface of each of the projections and the axis of the core member may gradually become small from the front end of each of the projections to the vertex of each of the projections. Still further, in a cross-sectional view taken along the axis of the core member, an angle formed between a tangent at an arbitrary point on the surface of each of the projections and the axis of the core member may gradually become small from the rear end of each of the projections to the vertex of each of the projections.

Still further, in a cross-sectional view taken along the axis of the core member, a tangent at the vertex of each of the projections and the axis of the core member are preferably substantially parallel to each other.

Still further, the surface-disposed member may be made of a fluorine-based polymer material.

Effects of the Invention

The present invention provides a wire member that exhibits excellent sliding property.

BRIEF DESCRIPTION OF THE DRAWINGS

FIG. 1 is a schematic enlarged main part side view of a wire member according to an embodiment of the present invention.

FIG. 2 is a schematic enlarged main part cross-sectional view taken along the axial direction of the wire member according to the embodiment of the present invention.

FIG. 3 is a further schematic enlarged cross-sectional view of FIG. 2.

FIG. 4 is a schematic cross-sectional view showing a midway state where a conventional wire member is inserted into a sleeve filled with liquid, the wire member being shifted from the right side to the left side in the drawing.

FIG. 5 is a schematic cross-sectional view showing a midway state where the wire member of the present invention is inserted into a sleeve filled with liquid, the wire member being shifted from the right side to the left side in the drawing.

FIG. 6 is a schematic cross-sectional view showing a midway state where the wire member of the present invention is inserted into the sleeve filled with liquid, the wire member being shifted from the right side to the left side in the drawing.

FIG. 7 is a schematic main part cross-sectional view showing a variation of the wire member of the present invention.

FIG. 8 is a schematic main part cross-sectional view showing a variation of the wire member of the present invention.

FIG. 9 is a schematic main part cross-sectional view showing a variation of the wire member of the present invention.

EMBODIMENT OF THE INVENTION

In the following, with reference to the accompanying drawings, a description will be given of a wire member according to an embodiment of the present invention. Note that, the drawings are partially scaled up or down for facilitating understanding of the structure. FIG. 1 is a schematic enlarged main part side view of a wire member 1 according to an embodiment of the present invention. FIG. 2 is a schematic enlarged main part cross-sectional view taken along the axial direction. The wire member 1 is elongated and flexible, and serves as a medical guide wire or a wire member 1 used in a manipulation system or a power transmission system of other various kinds of apparatuses and devices. As shown in FIGS. 1 and 2, the wire member 1 includes a core member 2 and a surface-disposed member 3.

The core member 2 is an elongated wire-like member, and structured to be flexible. The core member 2 may be made of any of various kinds of materials used for a core member of a conventional wire member 1. The core member 2 may be formed by any of various kinds of metal wire elements, for example, stainless steel, a piano wire, a cobalt-based alloy wire element, an alloy wire element that exhibits pseudoelasticity (including superelastic alloy), a steel wire, a brass wire, a copper wire, an aluminum wire and the like. In particular, in the case where the wire member 1 is structured as a medical guide wire, the core member 2 is preferably made of an alloy that exhibits pseudoelasticity (including superelastic alloy). Note that, the core member 2 may be formed by a wire-like member not being flexible.

The core member 2 made of cobalt-based alloy has a high elastic modulus and a proper elastic limit. Accordingly, the core member 2 made of cobalt-based alloy exhibits excellent torque transmissivity and hardly suffers from troubles such as buckling. Any cobalt-based alloy may be employed so long as the alloy contains Co as its constituent element. Alloy that contains Co as its main component (Co-based alloy:alloy that contains Co by the greatest ratio by weight among the elements structuring the alloy) is preferable, and Co—Ni—Cr-based alloy is more preferable. With the alloy of such a composition, the above-described effect becomes more pronounced. Further, the alloy of such a composition can undergo cold forming despite its high elastic modulus and high elastic limit. By virtue of its exhibiting high elastic limit, the core member 2 made of such alloy can be reduced in diameter while fully preventing buckling, and is fully flexible and rigid to be inserted into any predetermined site.

Further, the superelastic alloy is relatively soft and resilient, and less prone to be permanently curled. Thus, the core member 2 made of superelastic alloy provides the wire member 1 having high flexibility and resilience to bending. Thus, the wire member 1 excellently follows a blood vessel or the like that curves and bends in a complicated manner, offering the operator better operability. Further, the resilience of the core member 2 prevents the wire member 1 from being permanently curled despite repeated curving and bending deformation. Hence, a reduction in operability of the wire member 1 by permanently curling up with use can be prevented.

Further, the core member 2 may be in various modes. For example, in the case where the core member 2 is formed by a metal wire element, the core member 2 may be formed by a single metal wire. Alternatively, a single metal wire may be folded and twined to form the core member 2. Further, a plurality of metal wires may be twined to form the core member 2. Alternatively, a metal wire and a polymer wire-like member may be twined to form the core member 2. Still further, the central portion and the surface portion may be made of different materials. Still further, the entire surface of the core member 2 may be previously coated with a polymer material.

Further, when the core member 2 is formed by a metal wire element, the metal wire element may have a substantially constant outer diameter. Alternatively, the diameter may be partially enlarged or reduced. For example, when the tip portion of the core member 2 is tapered so that the outer diameter thereof reduces in the tip direction, the rigidity (flexural rigidity, torsional rigidity) of the core member 2 can be gradually reduced in the tip direction. As a result, excellent flexibility can be provided to the tip part of the wire member 1, and the wire member 1 is prevented from being folded or the like.

Further, the core member 2 may be formed by coupling, by welding or the like, a first core member part that structures the tip portion, and a second core member part that structures an intermediate portion and a proximal portion. When the core member 2 is structured by the first core member part and the second core member part, preferably the first core member part is set to have a smaller diameter than that of the second core member part. Further, the coupling portion is preferably tapered so that the first core member part and the second core member part are smoothly coupled to each other. With the core member 2 in such a structure also, the rigidity (flexural rigidity, torsional rigidity) of the core member 2 can be gradually reduced in the tip direction. As a result, the tip part of the wire member 1 becomes capable of passing through a narrow site in an excellent manner and becomes flexible. Thus, the wire member 1 is prevented from being folded or the like.

The surface-disposed member 3 is spirally disposed so as to leave predetermined spaces on the surface of the core member 2 along the longitudinal direction of the core member 2. The surface-disposed member 3 disposed on the core member 2 may be, for example, a wire element 31 that is thermally fusible to the core member 2. Such a wire element 31 may be made of any of various polymer materials. The polymer material may be, for example, a fluorine-based polymer material that exhibits lubricity. Such fluorine-based polymer may be, for example, tetrafluoroethylene-perfluoro (alkyl vinyl ether) copolymer (PFA, melting point 300 to 310° C.), polytetrafluoroethylene (PTFE, melting point 330° C.), tetrafluoroethylene-hexafluoropropylene copolymer (FEP, melting point 250 to 280° C.), ethylene-tetrafluoroethylene copolymer (ETFE, melting point 260 to 270° C.), polyvinylidene difluoride (PVDF, melting point 160 to 180° C.), polychlorotrifluoroethylene (PCTFE, melting point 210° C.), tetrafluoroethylene-hexafluoropropylene-perfluoroalkyl vinyl ether copolymer (EPE, melting point 290 to 300° C.) and the like, and hydrophobic polymer formed by fluorine-based polymer such as copolymer containing the foregoing polymers. Among others, PFA, PTFE, FEP, ETFE, and PVDF are preferable for their excellent sliding property.

Further, the wire element 31 may be a wire element formed by hydrophobic polymer such as polyamide, polyester, polycarbonate, urethane, silicone, polyethylene and polypropylene. Here, the polyester-based polymer is preferably aliphatic polyester-based polymer for its low fusing temperature. The aliphatic polyester-based polymer may be, for example, polyethylene succinate, polybutylene succinate, polyhexamethylene succinate, polyethylene adipate, polyhexamethylene adipate, polybutylene adipate, polyethylene oxalate, polybutylene oxalate, polyneopentyl oxalate, polyethylene sebacate, polybutylene sebacate, polyhexamethylene sebacate and the like which are obtained by polycondensation of glycol and aliphatic dicarboxylic acid. Further, the aliphatic polyester-based polymer may be, for example, poly($\alpha$-hydroxy acid) such as polyglycolic acid and polylactic acid, or copolymer of the foregoing, and aliphatic polyester such as poly($\omega$-hydroxyalkanoate) such as poly($\varepsilon$-caprolactone) and poly($\beta$-propiolactone), poly($\beta$-hydroxyalkanoate) such as poly(3-hydroxybutyrate), poly(3-hydroxyvalerate), poly(3-hydroxycaproate), poly(3-hydroxyheptanoate), poly(3-hydroxyoctanoate), and poly(4-hydroxybutyrate). Further, the polyamide-based polymer is more preferably aliphatic polyamide-based polymer for its low fusing temperature. Exemplary aliphatic polyamide-based polymer may be polyamide 12, polyamide 11, polyamide 6, and polyamide 66 or the like.

The method of manufacturing the wire element 31 from any of the above-described materials is not particularly limited. For example, any conventionally known method such as spinning the material by extrusion molding may be employed. Further, the method of wrapping the wire element 31 being the surface-disposed member 3 around the core member 2 is not particularly limited. For example, a method of wrapping the wire element 31 using a covering apparatus which is used in manufacturing covered yarns may be employed.

Further, the wire element 31 may be made of any single type of the foregoing polymer materials, or may be made of a combination of the polymer materials of different types. Further, the wire element 31 may be a solid wire, or may be a stranded wire formed by solid wires of an identical type being stranded with each other. Further, the wire element 31 may be a stranded wire formed by solid wires of different types being stranded with each other.

Further, the wire element 31 may be made of a material with which a melting point substantially does not exist and which instead shows Vicat softening temperature. Exemplary materials with which a melting point substantially does not exist and which instead show Vicat softening temperature include polyurethane and styrene-butadiene copolymer. The wire element 31 made of such materials starts to soften at Vicat softening temperature and can be fused to the core member 2.

The wire element 31 (the surface-disposed member 3) that is spirally wrapped around the surface of the core member 2 so as to leave predetermined spaces may be thermally fused and fixed to the core member 2 by, for example: heating the wire element 31 to a temperature around the melting point of the wire element 31 (or to a temperature around Vicat softening temperature), thereby melting (or softening) the wire element 31. The heating may be performed by, for example, externally applying heat to the wire element 31 wrapped around the core member 2, using a chamber-type thermal treatment apparatus. Further, with the core member 2 made of an electrically conductive material (a material that easily pass electricity) being highly resistive, the heating may be performed by applying voltage across the opposite ends of the core member 2 and thus achieving energizing heating.

Further, for example, when the core member 2 is made of an electrically conductive material and the wire element 31 is made of a material being lower in magnetism than the core member 2, the thermal fusing may be performed by electromagnetically induction heating the core member 2 with an electromagnetic induction heating apparatus from the outside of the wire element 31 disposed on the core member 2. Thus, the wire element 31 is melted (or softened) by heat of the heated core member 2, thereby thermally fusing to the core member 2. Note that, conceptually, a material being lower in magnetism than the core member 2 includes a material with no magnetism, in addition to a material being lower in magnetism than the core member 2. Note that, the electromagnetic induction heating is one scheme of heating which is introduced to electromagnetic cookers (IH cooking heaters), high-frequency welding and the like. The electromagnetic induction heating is based on the following principle. Alternating current is caused to flow through a coil, so that the magnetic field (the magnetic flux density) changes. By the change, an induced current (an eddy current) occurs in an electrically conductive substance placed in the magnetic field. Then, the electrically conductive substance itself generates heat by its resistance. Note that, setting a high frequency to the current flowing through the electromagnetic induction heating apparatus (alternating current flowing through the coil) can concentrate the heat generating sites in the core member 2 onto the surface of the core member 2. Conversely, setting a low frequency to the current allow the core member 2 to evenly generate heat from inside. Therefore, preferably the frequency of the current flowing through the electromagnetic induction heating apparatus can be changed as appropriate.

Note that, the wire element 31 can be heated by various known heating schemes such as heating by a far infrared heater and hot air blowing, apart from the above-described chamber-type thermal treatment, energizing heating, and electromagnetic induction heating.

Further, in order to more firmly fix the wire element 31 to the outer surface of the core member 2, preferably the following is performed. The core member 2 is formed with an adhesive agent such as primer being applied to its outer surface. Then, the wire element 31 is wrapped around the outer surface of the core member 2. Thereafter, by heating, the adhesive agent and the wire element 31 are melted.

By the heating process described above, the wire element 31 being the surface-disposed member 3 is fixed to the surface of the core member 2, to form projections 3A that project from the surface of the core member 2. As shown in FIG. 3 which is a schematic enlarged cross-sectional view taken along the axis of the core member 2, the projections 3A are disposed so as to leave predetermined spaces along the axial direction of the core member 2. Here, in a cross-sectional view taken along the axis of the core member 2, contact angles $\theta 1$ and $\theta 2$ respectively formed at the front end and rear end of each projection 3A of the wire element 31 being the surface-disposed member 3 relative to the surface of the core member 2 are each 5° or greater. Note that, the contact angles $\theta 1$ and $\theta 2$ are preferably each formed to fall within a numerical value range of 10° or greater. Further, the contact angles $\theta 1$ and $\theta 2$ are each formed to be 65° or smaller. Note that, the contact angles $\theta 1$ and $\theta 2$ are each more preferably formed to fall within a numerical value range of 55° or smaller. Here, the front end of the projection 3A refers to one end point of one projection 3A in the direction along the axis of the core member 2 in the contact region between the core member 2 and the projection 3A (the wire element 31) in a cross-sectional view taken along the axis. Further, the rear end of the projection 3A refers to other end point of the projection 3A in the direction along the axis of the core member 2 in the contact region between the core member 2 and the projection 3A (the wire element 31). Further, the contact angle $\theta 1$ formed at the front end of each projection 3A and the contact angle $\theta 2$ formed at the rear end of each projection 3A may be a substantially identical angle, or they may be different from each other so that the contact angle $\theta 1$ formed at the front end is greater than the contact angle $\theta 2$ formed at the rear end, so long as they fall within the above-described numerical value range.

Further, in the present embodiment, as shown in FIG. 2, in a cross-sectional view taken along the axis of the core member 2, the projections 3A on other side with reference to the core member 2 are disposed so as to oppose to the space regions 4 between the projections 3A disposed on one side with reference to the core member 2. When such a structure is employed, in a cross-sectional view taken along the axis of the core member 2, preferably the projections 3A are formed so that the vertex of each projection 3A disposed on other side with reference to the core member 2 is disposed so as to oppose to substantially the center of corresponding space region 4 in the axial direction of the core member 2.

Still further, in the present embodiment, in a cross-sectional view taken along the axis of the core member 2, the projections 3A are each substantially dome-shaped, so that the angle formed between a tangent at an arbitrary point on the surface of each projection 3A and the axis of the core member 2 gradually becomes small from the front end of each projection 3A toward its vertex, and so that, similarly in a cross-sectional view taken along the axis of the core member 2, the angle formed between a tangent at an arbitrary point on the surface of each projection 3A and the axis of the core member 2 gradually becomes small from the rear end of each projection 3A toward its vertex.

Still further, in the present embodiment, in a cross-sectional view taken along the axis of the core member 2, the surface of the core member 2 at the space regions 4 is substantially parallel to the axis of the core member 2. Still further, as shown in FIG. 2, in a cross-sectional view taken along the axis of the core member 2, the tangent at the vertex of each projection 3A and the axis of the core member 2 are substantially parallel to each other.

The wire member 1 according to the present embodiment can be manufactured by the simple method which includes: disposing the wire element 31 being the surface-disposed member 3 by spirally wrapping the wire element 31 around the surface of the core member 2; and performing heat treatment. Thus, a reduction in both time and costs of the manufacture is achieved.

Further, for example, when the wire member 1 according to the present embodiment is used as being inserted into a sleeve, by virtue of the wire member 1 having the wire element 31 (the surface-disposed member 3) that is disposed on the surface of the core member 2 and has lubricity, sliding resistance between the sleeve inner surface and the wire member 1 associated with the wire member 1 advancing or retracting inside the sleeve reduces, and a high sliding property is attained. In particular, when the wire element 31 (the surface-disposed member 3) is made of a fluorine-based polymer material, an even higher sliding property is attained. Further, since the wire element 31 spirally wrapped around the surface of the core member 2 forms the projections 3A that project from the surface of the core member 2 and the projections 3A are brought into contact with the inner surface of the sleeve, the contact area between the wire member 1 and the sleeve inner surface is largely reduced. This allows the wire member 1 to further smoothly advance or retract relative to the sleeve. In particular, as described above, in a cross-sectional view taken along the axis of the core member 2, when the projections 3A are formed so that the tangent at the vertex of each projection 3A and the axis of the core member 2 are substantially parallel to each other, the wire member 1 and the inner surface of the sleeve are in point contact at the vertex of each projection 3A. This provides an extremely high sliding property.

Further, when the wire member 1 of the present invention is used as being inserted into the sleeve which is filled with liquid such as physiological saline or a contrast medium, the resistance due to the fluid in the sleeve is largely reduced. In the following, a description will be given of the mechanism. Firstly, with reference to FIG. 4, a description will be given of the case where a conventional wire member 8 is inserted into the sleeve filled with liquid and advanced or retracted therein. FIG. 4 is a schematic cross-sectional view showing a midway state where the conventional wire member 8 is inserted into a sleeve 9 filled with liquid, and the conventional wire member 8 is shifted from the right side to the left side in the drawing. Note that, since the shifting wire member 8 is represented as a static system, FIG. 4 illustrates the liquid in the sleeve 9 as flowing from the left side to the right side as indicated by "→". As shown in FIG. 4, when the conventional wire member 8 is shifted inside the sleeve 9 filled with liquid, on the rear side of each projection 81 of the wire member 8 (herein the shifting direction of the wire member 8 is defined as the front side), the flow of the liquid is separated, and a large eddy is formed. When such flow separation (eddy) is formed, pressure drops in the separation region (the eddy region), increasing the difference in pressure between the front side and the rear side of each projection 81 and pressure drag. As a result, large resistance acts on the shifting wire member 8, preventing the wire member 8 from smoothly shifting in the sleeve.

On the other hand, as to the wire member 1 of the present invention, in a cross-sectional view taken along the axis of the core member 2, the projections 3A formed by the surface-disposed member 3 are formed so that the contact angles $\theta 1$ and $\theta 2$ respectively formed at the front end and the rear end of each projection 3A relative to the surface of the core member 2 are each 5° or greater. Therefore, as shown in FIG. 5, flow separation is less prone to occur on the rear side of each projection 3A (herein the shifting direction is defined as the front side). Thus, no large eddy is formed, and liquid flowing over each projection 3A forms regular flow along the surface of each projection 3A and the surface of each space region 4 between the projections 3A. This reduces pressure drag between the front side and the rear side of each projection 3A, and allows the wire member 1 to smoothly advance or retract in the sleeve 9. Note that, each projection 3A is preferably formed so that the contact angles θ1 and θ2 each become 65° or smaller. With the contact angles θ1 and θ2 each being greater than 65°, the projections 3A (the wire element 31) tend to be separated from the surface of the core member 2 or caught by any projecting portion, which is not preferable. Further, with the contact angles θ1 and θ2 each being smaller than 5°, the projections 3A and the inner surface of the sleeve 9 are less prone to be brought into point contact with each other. This may restrict the sliding property improving effect and hence is not preferable. Further, in order to realize further smooth advancing and retracting of the wire member 1 relative to the sleeve 9, each projection 3A is preferably formed so that the contact angles θ1 and θ2 each become 10° or greater. Further, in order to effectively suppress occurrence of flow separation, each projection 3A is more preferably formed so that the contact angles θ1 and θ2 each become 55° or smaller. Here, similarly to FIG. 4, FIG. 5 is a schematic cross-sectional view showing a midway state where the wire member 1 of the present invention is shifted in the sleeve 9 from the right side to the left side in the drawing. Further, the shifting wire member 1 is represented as a static system, with the liquid in the sleeve 9 being illustrated to flow from the left side to the right side as indicated by "→".

Further, when the wire member 1 of the present invention is used as being inserted into the sleeve 9 which is filled with liquid such as physiological saline or a contrast medium, the projections 3A at the wire member 1 effectively suppress contact between the wire member 1 and the inner wall of the sleeve 9, achieving even more higher sliding property. Specifically, as described above, as to the wire member 1 of the present invention, the surface-disposed member 3 is spirally disposed on the surface of the core member 2. Accordingly, on the surface of the wire member 1, the projections 3A and the space regions 4 are alternately disposed along the longitudinal direction of the core member 2. Further, each projection 3A is formed so that the contact angles θ1 and θ2 respectively formed at the front end and the rear end of each projection 3A relative to the surface of the core member 2 assume the above-noted values. Such a structure allows the wire member 1 to shift in the sleeve 9 filled with liquid, with the axis of the wire member 1 (the axis of the core member 2) and the axis of the sleeve 9 being substantially overlaid on each other. As a result, the wire member 1 becomes capable of shifting while maintaining a substantially uniform clearance between the surface-disposed member 3 (the projections 3A) of the wire member 1 and the inner wall of the sleeve 9.

In the following, with reference to FIG. 6, a detailed description will be given of the above-described effect. Similarly to FIG. 5, FIG. 6 is a schematic cross-sectional view showing a midway state where the wire member 1 of the present invention is shifted in the sleeve 9 from the right side to the left side in the drawing. Further, the shifting wire member 1 is represented as a static system, with the liquid in the sleeve 9 being illustrated to flow from the left side to the right side as indicated by "→". Firstly, as described above, when the wire member 1 of the present invention is shifted in the sleeve 9 filled with liquid, flow separation is less prone to occur on the rear side of each projection 3A (herein the shifting direction is defined as the front side). Thus, liquid flowing over each projection 3A forms regular flow along the surface of each projection 3A and the surface of each space region 4 between the projections 3A (a streamline conforming to the surface of each projection 3A and the surface of each space region 4 between the projections 3A is formed). By virtue of such flow being realized, the flow velocity of liquid being flowing over each projection 3A becomes constant near the surface of each projection 3A. Similarly, the flow velocity of liquid near the surface of the core member 2 at each space region 4 between the projections 3A becomes constant. As can also be derived from the Bernoulli theorem of hydrodynamics, since the flow velocity near the surface of each projection 3A becomes faster than the flow velocity near the surface of the core member 2 at the space regions 4, the pressure acting on the surface of the projection 3A becomes smaller than the pressure acting on the surface of the core member 2 at the space regions 4. That is, as shown in FIG. 6, when the wire member 1 of the present invention is shifted as being inserted into the sleeve 9 filled with liquid, the pressure acting on the surface of the wire member 1 is distributed in alternating high and low values along the longitudinal direction of the wire member 1.

Further, with the wire member 1 of the present invention, in a cross-sectional view taken along the axis of the core member 2, the projections 3A on other side with reference to the core member 2 are disposed so as to oppose to the space regions 4 each formed between the projections 3A disposed on one side with reference to the core member 2. Here, focusing on a pair of projection 3A and space region 4 disposed so as to oppose to each other with reference to the core member 2, as shown in FIG. 6, pressure is low on the projection 3A side while pressure is high on the space region 4 side. The above-described structure creates such a pressure distribution in which high and low pressures are alternately and sequentially repeated along the longitudinal direction of the wire member 1. Further, focusing again on a pair of projection 3A and space region 4 disposed so as to oppose to each other with reference to the core member 2, the pressure difference is formed with reference to the core member 2. As a result, while the wire member 1 receives force from the high-pressure space region 4 side toward the projection 3A opposing to the space region 4, the direction of this force is alternately repeatedly reversed along the longitudinal direction of the wire member 1.

As to the wire member 1 receiving the above-described force, a description will be given of the movement of the wire member 1 with reference to an arbitrary point Z of the sleeve 9 in FIG. 6. The wire member 1 shifting away from the arbitrary point Z shifts toward the arbitrary point Z next moment by its shifting in the sleeve 9. As a result of this behavior being repeated, the wire member 1 can shift in the sleeve 9 with the axis of the wire member 1 (the axis of the core member 2) and the axis of the sleeve 9 being substantially overlaid on each other. Thus, the wire member 1 becomes capable of shifting while maintaining a substantially uniform clearance between the surface-disposed member 3 (the projections 3A) of the wire member 1 and the inner wall of the sleeve 9.

In the foregoing, while the description has been given of the wire member 1 of the present invention, the specific structure is not limited to the above-described embodiment. In the above-described embodiment, as shown in FIG. 3, in a cross-sectional view taken along the axis of the core member 2, the projections 3A are each substantially dome-shaped, so that the angle formed between a tangent at an arbitrary point on the surface of each projection 3A and the axis of the core member 2 gradually becomes small from the front end of each projection 3A toward its vertex, and so that, similarly in a cross-sectional view taken along the axis of the core member 2, the angle formed between a tangent at an arbitrary point on the surface of each projection 3A and the axis of the core member 2 gradually becomes small from the rear end of each projection 3A toward its vertex. However, the present invention is not limited to such a structure. For example, as shown in FIG. 7, in a cross-sectional view taken along the axis of the core member 2, the projections 3A may be shaped so that the angle formed between a tangent at an arbitrary point on the surface of each projection 3A and the axis of the core member 2 gradually becomes small from the front end of each projection 3A toward its vertex, and so that, similarly in a cross-sectional view taken along the axis of the core member 2, the angle formed between a tangent at an arbitrary point on the surface of each projection 3A and the axis of the core member 2 becomes substantially constant from the rear end of each projection 3A toward its vertex.

Further, for example as shown in FIG. 8, in a cross-sectional view taken along the axis of the core member 2, the projections 3A may be shaped so that the angle formed between a tangent at an arbitrary point on the surface of each projection 3A and the axis of the core member 2 gradually becomes small from the rear end of each projection 3A toward the vertex, and so that, similarly in a cross-sectional view taken along the axis of the core member 2, the angle formed between a tangent at an arbitrary point on the surface of each projection 3A and the axis of the core member 2 becomes substantially constant from the front end of the projection 3A toward its vertex.

Alternatively, as shown in FIG. 9, in a cross-sectional view taken along the axis of the core member 2, the projections 3A may be shaped so that the angle formed between a tangent at an arbitrary point on the surface of each projection 3A and the axis of the core member 2 becomes substantially constant from the front end of each projection 3A toward its vertex, and so that, similarly in a cross-sectional view taken along the axis of the core member 2, the angle formed between a tangent at an arbitrary point on the surface of each projection 3A and the axis of the core member 2 becomes substantially constant from the rear end of the projection 3A toward its vertex. In such a structure, each projection 3A is formed to be triangular in which the angle formed between a tangent at an arbitrary point on the surface of each projection 3A and the axis of the core member 2 is substantially identical to the contact angle formed at the front end of each projection 3A in a range from the front end of each projection 3A toward the vertex, and the angle formed between a tangent at an arbitrary point on the surface of each projection 3A and the axis of the core member 2 is substantially identical to the contact angle formed at the rear end of each projection 3A in a range from the rear end of each projection 3A toward the vertex.

Further, in the above-described embodiment, the wire member 1 is structured by: employing the wire element 31 as the surface-disposed member 3; spirally wrapping the wire element 31 around the surface of the core member 2; and thereafter subjecting the wire element 31 and the core member 2 to a predetermined thermal treatment. However, the present invention is not particularly limited to such a structure. For example, the wire member 1 may be structured by: covering the surface of the core member 2 with a tubular body made of thermoplastic resin; thereafter subjecting the tubular body to press work using a predetermined mold assembly while heating the tubular body, to mold the surface-disposed member 3 having the projections 3A in the above-described predetermined shape on the surface of the core member 2. Further, the surface-disposed member 3 having the projections 3A in the above-described predetermined shape may be formed by subjecting the surface of the tubular body covering the surface of the core member 2 to cutting work.

DESCRIPTION OF REFERENCE SIGNS 1 wire member
2 core member
3 surface-disposed member
3A projection
31 wire element
4 space region
9 sleeve
θ1 contact angle formed at the front end of projection 3A relative to the surface of core member 2
θ2 contact angle formed at the rear end of projection 3A relative to the surface of core member 2

The invention claimed is:

1. A wire member comprising:
a core member that has an elongated shape; and
a surface-disposed member that is spirally disposed on a surface of the core member so as to leave predetermined spaces along a longitudinal direction of the core member, wherein
in a cross-sectional view taken along an axis of the core member, a front end and a rear end of each of projections formed by the surface-disposed member each form a contact angle falling within a range of 5° to 65° inclusive relative to the surface of the core member,
in the cross-sectional view taken along the axis of the core member, an angle formed between a tangent at an arbitrary point on a surface of each of the projections and the axis of the core member gradually becomes small from the front end of each of the projections to the vertex of each of the projections,
in the cross-sectional view taken along the axis of the core member, the surface-disposed member has a dome shape where a surface of the dome shape is smoothly curved to form the dome-shaped projection,
in the cross-sectional view taken along the axis of the core member, the dome-shaped projection has a contact area where the dome-shaped projection is in contact with the surface of the core member, and the contact area of each of the dome-shaped projections of the surface-disposed member has a front end and a rear end which are opposite to each other in the longitudinal direction of the core member, the contact angle of the surface-disposed member at each of the front and rear ends of the contact area falling within a range of 5° to 65° inclusive relative to the surface of the core member,
in the cross-sectional view taken along the axis of the core member, the angle formed between the tangent on the surface of each of the projections and the axis of the core member continuously decreases from the front end of the contact area at each of the projections to the vertex of each of the projections, and
in the cross-sectional view taken along the axis of the core member, the angle formed between the tangent on the surface of each of the projections and the axis of the core member continuously decreases from the rear end of the contact area at each of the projections to the vertex of each of the projections.

2. The wire member according to claim 1, wherein the surface-disposed member is made of a fluorine-based polymer material.

3. The wire member according to claim 1, wherein in the cross-sectional view taken along the axis of the core member, a tangent at the vertex of each of the projections and the axis of the core member are substantially parallel to each other.

4. A wire member comprising:
a core member that has an elongated shape; and
a surface-disposed member that is spirally disposed on a surface of the core member so as to leave predetermined spaces along a longitudinal direction of the core member, wherein
in a cross-sectional view taken along an axis of the core member, a front end and a rear end of each of projections formed by the surface-disposed member each form a contact angle falling within a range of 5° to 65° inclusive relative to the surface of the core member,
in the cross-sectional view taken along the axis of the core member, the projections on other side with reference to the core member are disposed so as to oppose to space regions each formed between the projections disposed on one side with reference to the core member,
in the cross-sectional view taken along the axis of the core member, a vertex of each of the projections on other side with reference to the core member is disposed so as to oppose to substantially a center of corresponding one of the space regions in an axial direction of the core member,
in the cross-sectional view taken along the axis of the core member, the surface-disposed member has a dome shape where a surface of the dome shape is smoothly curved to form the dome-shaped projection,
in the cross-sectional view taken along the axis of the core member, the dome-shaped projection has a contact area where the dome-shaped projection is in contact with the surface of the core member, and the contact area of each of the dome-shaped projections of the surface-disposed member has a front end and a rear end which are opposite to each other in the longitudinal direction of the core member, the contact angle of the surface-disposed member at each of the front and rear ends of the contact area falling within a range of 5° to 65° inclusive relative to the surface of the core member,
in the cross-sectional view taken along the axis of the core member, the angle formed between the tangent on the surface of each of the projections and the axis of the core member continuously decreases from the front end of the contact area at each of the projections to the vertex of each of the projections, and
in the cross-sectional view taken along the axis of the core member, the angle formed between the tangent on the surface of each of the projections and the axis of the core member continuously decreases from the rear end of the contact area at each of the projections to the vertex of each of the projections.

5. The wire member according to claim 4, wherein in the cross-sectional view taken along the axis of the core member, a surface of the core member at the space regions is substantially parallel to the axis of the core member.

6. A wire member comprising:
a core member that has an elongated shape; and
a surface-disposed member that is made of a fluorine-based polymer material and spirally disposed on a surface of the core member so as to leave predetermined spaces along a longitudinal direction of the core member, wherein
in a cross-sectional view taken along an axis of the core member, a front end and a rear end of each of projections formed by the surface-disposed member each form a contact angle falling within a range of 5° to 65° inclusive relative to the surface of the core member,
in the cross-sectional view taken along the axis of the core member, the projections on other side with reference to the core member are disposed so as to oppose to space regions each formed between the projections disposed on one side with reference to the core member,
in the cross-sectional view taken along the axis of the core member, a vertex of each of the projections on other side with reference to the core member is disposed so as to oppose to substantially a center of corresponding one of the space regions in an axial direction of the core member,
in the cross-sectional view taken along the axis of the core member, the surface-disposed member has a dome shape where a surface of the dome shape is smoothly curved to form the dome-shaped projection,
in the cross-sectional view taken along the axis of the core member, the dome-shaped projection has a contact area where the dome-shaped projection is in contact with the surface of the core member, and the contact area of each of the dome-shaped projections of the surface-disposed member has a front end and a rear end which are opposite to each other in the longitudinal direction of the core member, the contact angle of the surface-disposed member at each of the front and rear ends of the contact area falling within a range of 5° to 65° inclusive relative to the surface of the core member,
in the cross-sectional view taken along the axis of the core member, the angle formed between the tangent on the surface of each of the projections and the axis of the core member continuously decreases from the front end of the contact area at each of the projections to the vertex of each of the projections, and
in the cross-sectional view taken along the axis of the core member, the angle formed between the tangent on the surface of each of the projections and the axis of the core member continuously decreases from the rear end of the contact area at each of the projections to the vertex of each of the projections.

\* \* \* \* \*